United States Patent
Frank

(10) Patent No.: US 7,329,231 B2
(45) Date of Patent: Feb. 12, 2008

(54) DOME-SHAPED BACK BRACE

(76) Inventor: William Frank, 665 Old Pond La., Powell, OH (US) 43065

( * ) Notice: Subject to any disclaimer, the term of this patent is extended or adjusted under 35 U.S.C. 154(b) by 427 days.

(21) Appl. No.: 10/908,570

(22) Filed: May 17, 2005

(65) Prior Publication Data

US 2006/0264791 A1    Nov. 23, 2006

(51) Int. Cl.
A61F 5/00    (2006.01)
(52) U.S. Cl. .................. 602/19; 128/96.1; 128/115.1
(58) Field of Classification Search .............. 602/19, 602/5; 128/96.1, 100.1, 115.1, 846, 845, 128/876, 875, 874; 2/311, 312, 338; 482/106
See application file for complete search history.

(56) References Cited

U.S. PATENT DOCUMENTS

| | | | |
|---|---|---|---|
| 1,174,757 A * | 3/1916 | Packer ........................ 602/19 |
| 3,871,367 A | 3/1975 | Miller | |
| 4,173,973 A | 11/1979 | Hendricks | |
| 4,508,110 A | 4/1985 | Modglin | |
| 4,541,419 A | 9/1985 | Osawa | |
| 4,572,167 A | 2/1986 | Brunswick | |
| 4,905,993 A * | 3/1990 | Barone ........................ 482/106 |
| 5,074,292 A | 12/1991 | Cox | |
| 5,232,424 A * | 8/1993 | Pearson et al. ............. 482/106 |
| 5,267,947 A * | 12/1993 | James et al. .................. 602/19 |
| 5,310,401 A * | 5/1994 | Striano ........................ 602/19 |
| 5,433,697 A | 7/1995 | Cox | |
| 5,520,624 A * | 5/1996 | Amato ........................ 602/19 |
| 5,547,462 A * | 8/1996 | Lanigan et al. ............... 602/19 |
| 6,099,490 A * | 8/2000 | Turtzo ........................ 602/19 |
| 6,623,419 B1 * | 9/2003 | Smith et al. .................. 600/15 |

* cited by examiner

*Primary Examiner*—Kim M Lewis
(74) *Attorney, Agent, or Firm*—Malin, Haley & DiMaggio, P.A.

(57) ABSTRACT

A brace for supporting both the abdomen and lower back of the user. The brace includes a preformed abdominal support member and a preformed lumbar support member having an ideal lumbar shape with a circular dome that is vertically bisected by an oblong, elliptical protrusion, the support members each joined by two belts. The belts are positioned through slots on each member and are used to select the biasing force needed for each user. The device further includes rounded corners with indented edges and surface vents on each support member for the user's comfort during sporting events or strenuous activity.

4 Claims, 6 Drawing Sheets

DOME-SHAPED BACK BRACE

FIELD OF THE INVENTION

This invention relates to a two-component brace primarily intended for providing immobilization of the human back and more particularly to a brace for providing an ideal back profile and simultaneous abdominal and lumbar support to the user to realign and tone muscles around the back and stomach.

DESCRIPTION OF RELATED ART

Spinal and lower back muscular pain is a common problem in many individuals. This type of pain, particularly among older or overweight individuals, can easily be aggravated during any type of body trauma such as heavy lifting or strenuous physical activity.

Prescription drugs, which are not always effective, must often be used to alleviate lower back pain. Day-to-day activity requires movement of the back, which can lead to further muscular aggravation that requires use of the most potent pain relief medications to produce any positive result.

To help alleviate lower back pain, prevent injury or aid in recovery, a device that can provide support to the lower back to prevent muscular strain must be used. In the past, many types of devices have been created to help with this problem. These devices range from wrap-type supports to individual solid support fixtures placed longitudinally along the back to restrain movement. Many of these devices are either very heavy, too hot to wear, burdensome by unduly restricting movement, or do not provide the proper back support and alignment to be useful.

Recent research has determined that the most effective lumbar support occurs when the abdominal area of the user is supported as well. U.S. Pat. No. 4,572,167, issued to Brunswick on Feb. 25, 1986, and U.S. Pat. No. 4,508,110, issued to Modglin on Apr. 2, 1985, describe support devices which wrap around the user's body but do not provide adequate abdominal and lumbar support due to the flexibility of the material used in construction and the methods of attachment. U.S. Pat. No. 4,173,973, issued to Hendricks on Nov. 13, 1979, U.S. Pat. No. 4,541,419, issued to Osawa on Sep. 17, 1985 and U.S. Pat. No. 3,871,367, issued to Miller on Mar. 18, 1975, describe devices which are awkward to wear and are incapable of simultaneous abdominal and lumbar support. U.S. Pat. No. 5,074,292, issued to Cox on Dec. 24, 1991, shows a back brace that can be form fitted to the individual. Although the '292 device worked well, the present invention is a substantial improvement over the prior art that uses an ideal lumbar configuration for improved muscle support. U.S. Pat. No. 5,433,697 issued to Cox Jul. 18, 1995 shows a conformable back brace with abdominal support that uses a dome as a preformed lumbar support member having an ideal lumbar shape. Although the device shown in the '697 is a good back support that uses a hemispherical lumbar support, the present invention provides a substantial improvement with its different lumbar support configuration.

Thus, this review of the prior art reveals the need for a device to provide simultaneous lumbar and abdominal support and alignment that is also lightweight, comfortable, and easily adjustable. The device should also lend itself to being worn not only while sedentary, such as sitting for long periods in the workplace, but also during strenuous physical activity such as physical work, golf, tennis, or other sports.

SUMMARY OF THE INVENTION

The present invention relates to a two-component brace which includes both an abdominal support and a lumbar support member. Each member is manufactured from a preformed plastic that is shaped as an ideal body contour for the respective area of the body to be supported. The lumbar support member includes a strategically-shaped center dome for supporting the lower lumbar back region to provide ideal back curvature and alignment of lumbar muscles and the spine. In view of the substantially thin size of the brace, the brace can easily be worn within or outside a user's clothing.

Each support member includes rounded edges which are tapered for a comfortable fit along with one or more torso-encompassing belt adjustment slots positioned at each end of each member. These slots are used to engage separate fastening belts on each end thereof. Each belt is made of a durable lightweight fabric having some elasticity with hook and loop fastener materials secured thereto. Each end of each belt is then positioned through a selected one of the plurality of adjustment slots on each support member where each belt, engages with itself, to form small loops at each respective end. This enables both the abdominal and lumbar support members to be engaged separately to hold and shape both of the members firmly against the user. Additionally, a plurality of holes is placed about each support surface to allow body heat to escape from under the support members.

The lumbar support device has a mid-portion that is fairly flat or just slightly curved, with a central dome area that has a circular dome vertically bisected by an oblong elliptical protrusion of equal height raised to face convexly when pressed against the lower lumbar region of the user. The dome rises to a height of approximately one-fourth inch above the planar portion of the surface and is approximately 2¾ inches in diameter. In addition, the dome is centrally located on the support member. The ends of the lumbar support member are curved as they would reach around the body of the user and include tapered end portions for comfort when the device is pulled tight around the user. With the dome convex protrusions, the overall shape of the lumbar support member is designed to provide an ideal back configuration so that the user's muscles and spine are appropriately aligned. Continued use of the device allows the user's muscles to achieve close to an ideal conditioning and toning.

The front abdominal support member is curved much as the front of the body is curved to provide a flush support area. The abdominal support member is also quite large, extending at least 5 inches in height and approximately 12 inches in overall length to extend to the outer edges of the abdominal area of the body.

The two adjustment bands include elasticized portions of connective material to provide some elasticity when wearing the device fairly tightly so as not to impede normal body movement by the wearer. In fact, a wearer can participate in sports, such as golf, that require substantial body movement during play, and in this way, the apparatus is not confining to the user.

Adjustment for various sized individuals is also accomplished so that the device can be worn flush to provide proper body support and configuration, both in the lumbar region and in the front abdominal region, by having fabric hook and loop fasteners that allow individualized adjustment along the straps on each side with the variable adjustment slots as provided. The overall fit can be somewhat universal, accommodating waist sizes 25 inches to 54 inches with the radius of curvature of the support members being approximately 8½ inches.

By using the preformed ideal lumbar support, in which the convex dome area nestles in the lower lumbar region of the back in conjunction with the abdominal front support, alignment and toning of the muscles is achieved for greater comfort while wearing the brace. The brace also alleviates muscle strain by providing the abdominal region with contractive muscular support with the overall effect of greatly reducing strain on the lower back area.

An object of this invention is to provide a lightweight, comfortable back support member that does not restrict the movement of the user and that is not to too hot to wear.

Another object of this invention is to provide a lightweight, comfortable back support that includes an abdominal support member for enhancing the functionality and effectiveness of the lumbar back support member.

Still another object of this invention is to provide a lumbar back support member that can be worn by a user while sedentary and while performing strenuous physical activity, including sports.

Yet another object of this invention is to provide a lumbar back support member that provides strong support for the proper alignment of the user's lumbar and abdominal muscles as well as the user's spine.

In accordance with these and other objects which will become apparent hereinafter, the instant invention will now be described with particular reference to the accompanying drawings.

DETAILED DESCRIPTION

Figure 1:
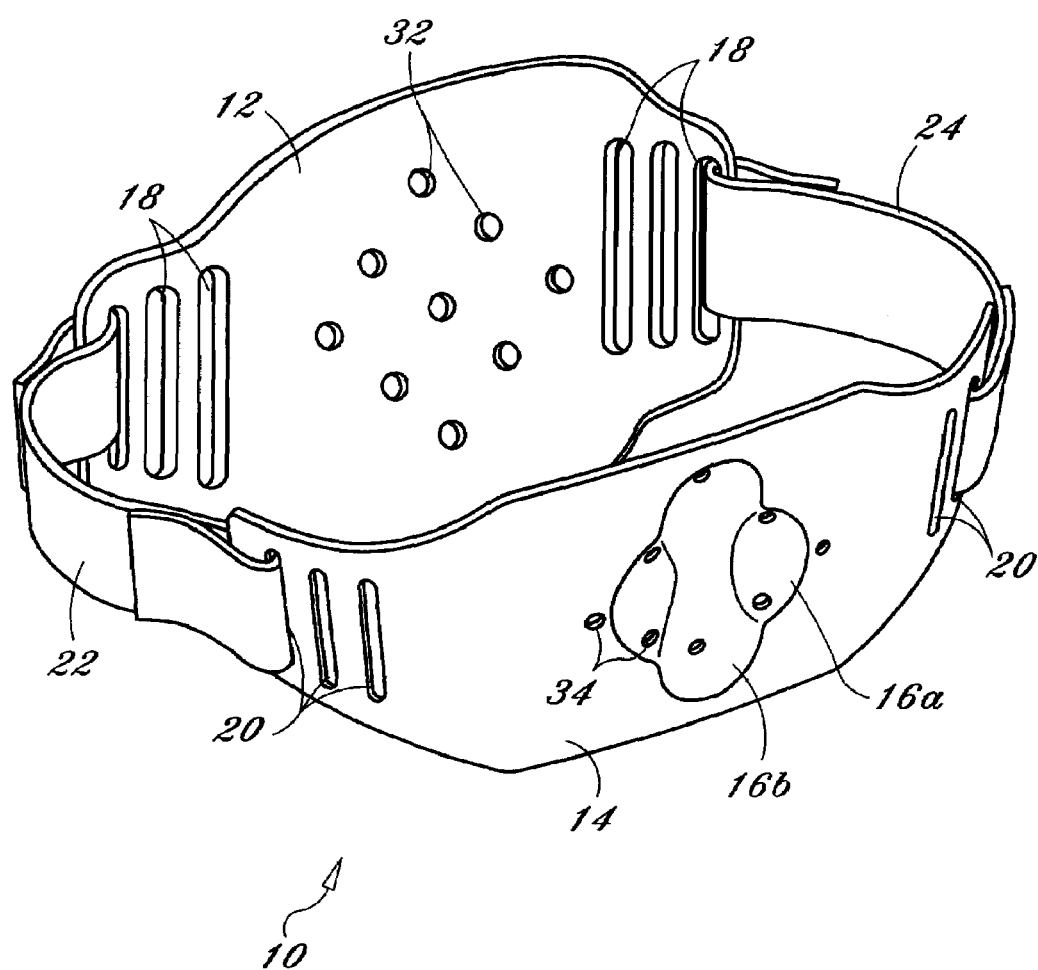
FIG. 1 illustrates a back perspective view of the invention, the support members being transparent plastic.

With reference to FIGS. 1-6, a two-component back brace with abdominal and lumbar support members is generally shown at 10. The invention 10 includes an abdominal support member 12 and a lumbar support member 14. FIGS. 3A and 3B show sectional views of the abdominal support member 12 while FIGS. 4A and 4B show sectional views of the lumbar support member 14. Although both the abdominal support member 12 and lumbar support member 14 are generally convex in shape to conform to a peripheral torso shape of a human being in front and back body areas, the lumbar support member 14 includes a centrally-positioned convex, hemispherical dome 16a bisected vertically through its center by an oblong elliptical protrusion 16b of equal height. Said dome 16a and elliptical protrusion 16b are located substantially at the center of the lumbar support member 14. The dome 16a protrudes into a lower central lumbar back region of a wearer to provide the ideal human back contour and extends longitudinally across the surface of the lower back. As illustrated in FIGS. 4A and 4B, the central dome 16a and elliptical protrusion 16b of said lumbar support member 14 extend inwardly at the back's lower lumbar region.

The lumbar region of the lower back is often the most difficult to support due to its shape. A major advantage to the instant invention is the type of material and the specific dome shape used to conform both the abdominal and lumbar support members 12, 14 to the various body shapes and sizes of all users. First, in the preferred embodiment, both the abdominal support member 12 and lumbar support member 14 are manufactured from VIVAK® Thermoplastic approximately one-sixteenth inch thick. Each lumbar support 14 is pre-molded to a predetermined ideal shape of a perfect back, in small, medium and large sizes.

Both the abdominal support member 12 and lumbar support member 14 include at least three vertical slots, 18 and 20 respectively, which are positioned at each end of the members. Said slots 18 and 20 have a sufficient width and height to accommodate left and right fastening belts 22 and 24 to bias the support members 12, 14 snugly against the user. One slot 18, 20 at each end of each support member 12, 14 is selected to fit said support members 12, 14 properly around the torso of the wearer. This engagement configuration allows the fastening belts 22, 24 to move within the respective slots 18, 20 of said fastening belts to permit easier adjustment of the belts when in use. Overall, the slots 18 and 20 allow for a wide range of movement to accommodate various sizes of users.

Figure 2:
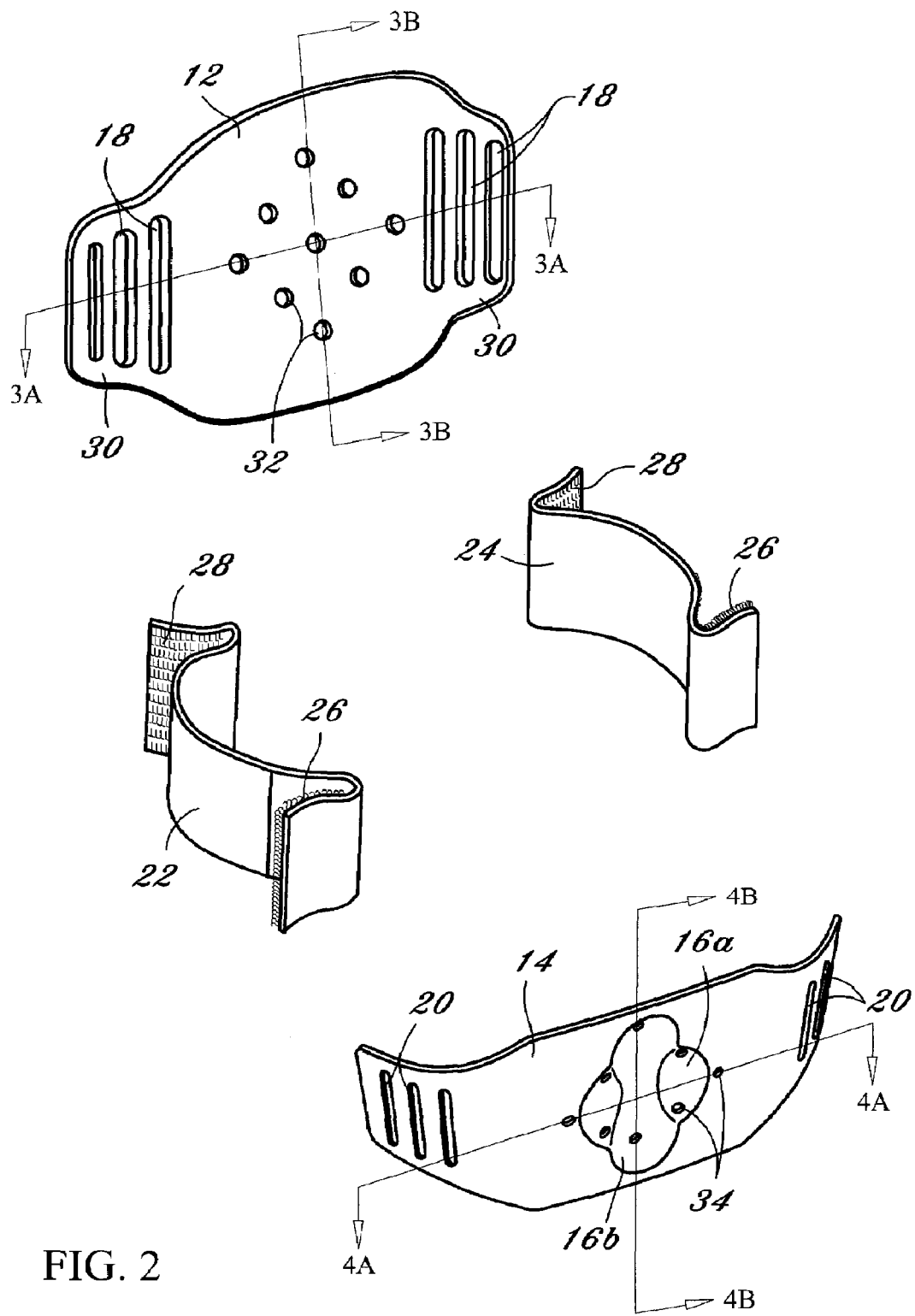
FIG. 2 illustrates a back exploded perspective view of that shown in FIG. 1.

As seen in FIG. 2, the left fastening belt 22 and right fastening belt 24 are made preferably from a lightweight, heavy-duty nylon, which aids in making the device comfortable to wear. Each belt 22 and 24 includes hook-fastening material 26 and loop-fastening material 28 secured at each end to securely hold each belt, through one of the plurality of adjustment slots 18 and 20, upon itself. FIG. 1 illustrates each end of each belt 22 and 24 folded back upon itself forming a small loop. Although hook and loop material 26 and 28 is used in the preferred embodiment, those skilled in the art will recognize that any type of rigid fasteners, such as snaps or the like, could be used.

Additionally, both the abdominal support member 12 and lumbar support member 14 are substantially rectangular in shape and include rounded corners 30 that are tapered. The rounded, tapered corners 30 of said support members 12 and 14 enable the user to securely fasten the brace 10 around the torso, applying as much biasing force as needed using the left and/or right fastening belts 22, 24 without unwanted forces pressing into the user's body. Without these tapered end corners 30, the brace 10 would quickly become uncomfortable due to excessive force applied at these pressure points.

Finally, the abdominal support member 12 and the lumbar support member 14 include a plurality of abdominal support and lumbar support vents 32 and 34. Said abdominal support vents 32 and lumbar support vents 34 prevent an excess buildup of body heat under each support member 12, 14 and allow air to circulate under each respective support member when needed most, viz. exercise or strenuous activity.

Figure 3A:
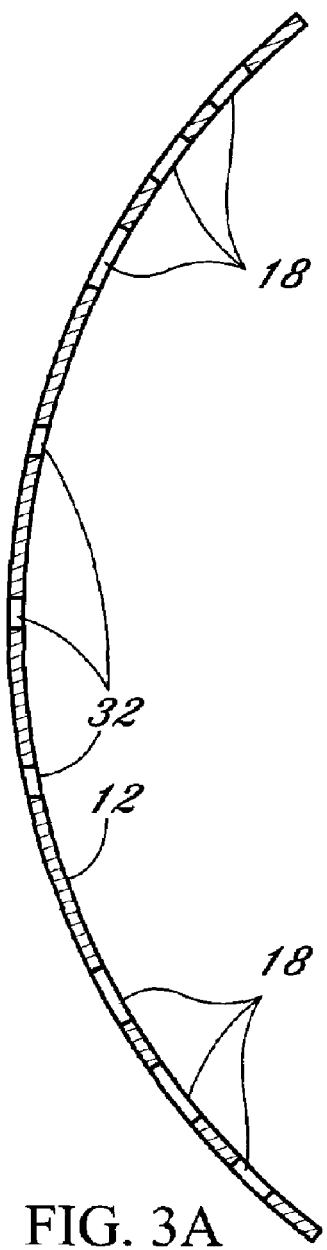
FIGS. 3A and 3B illustrate cross-sectional views of the abdominal support member shown through lines 3B-3A and 3B-3B shown in FIG. 2, respectively.
Figure 3B:
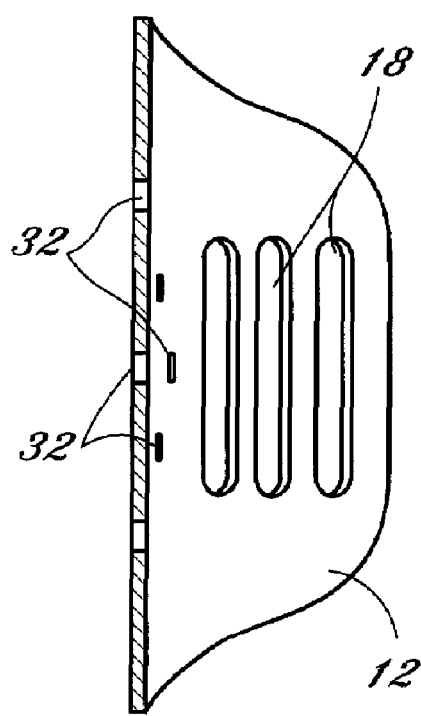
Figure 4A:
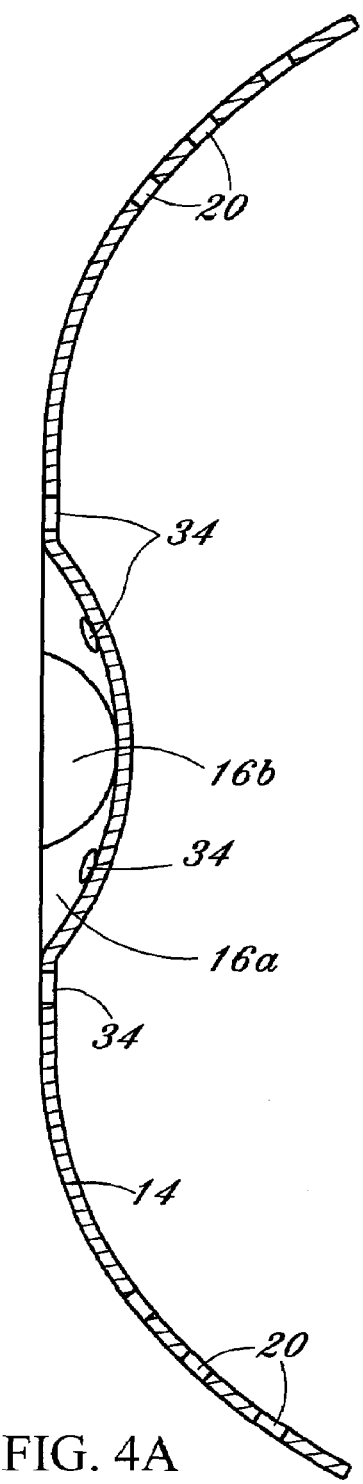
FIGS. 4A and 4B illustrate cross-sectional views of the lumbar support member shown through lines 4A-4A and 4B-4B shown in FIG. 2, respectively.
Figure 4B:
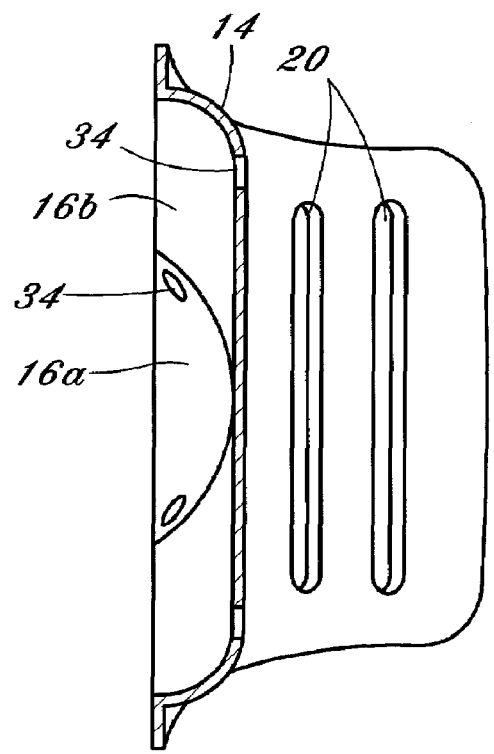
Figure 5:
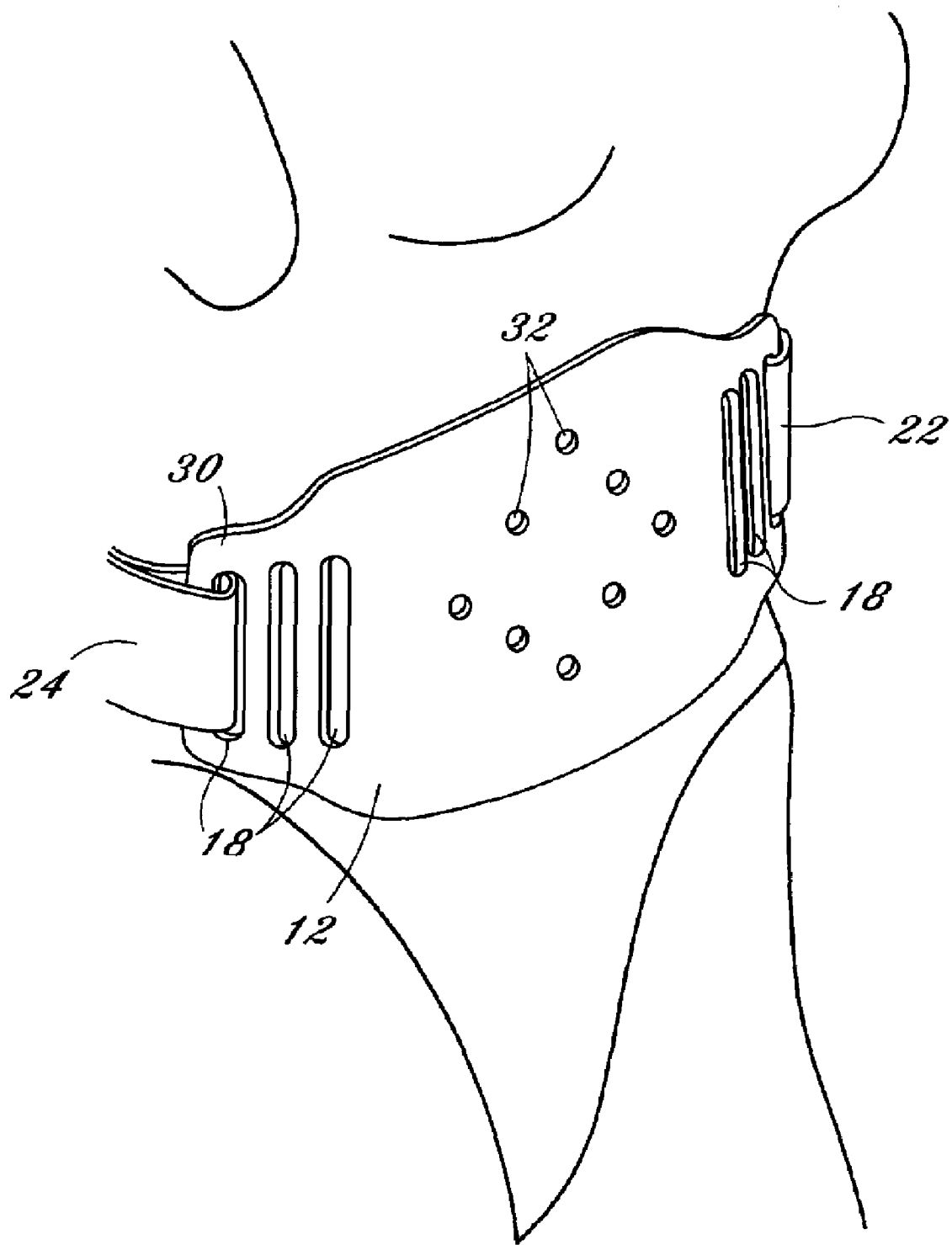
FIG. 5 illustrates a front perspective view of the abdominal support member as positioned on the abdomen of the user.
Figure 6:
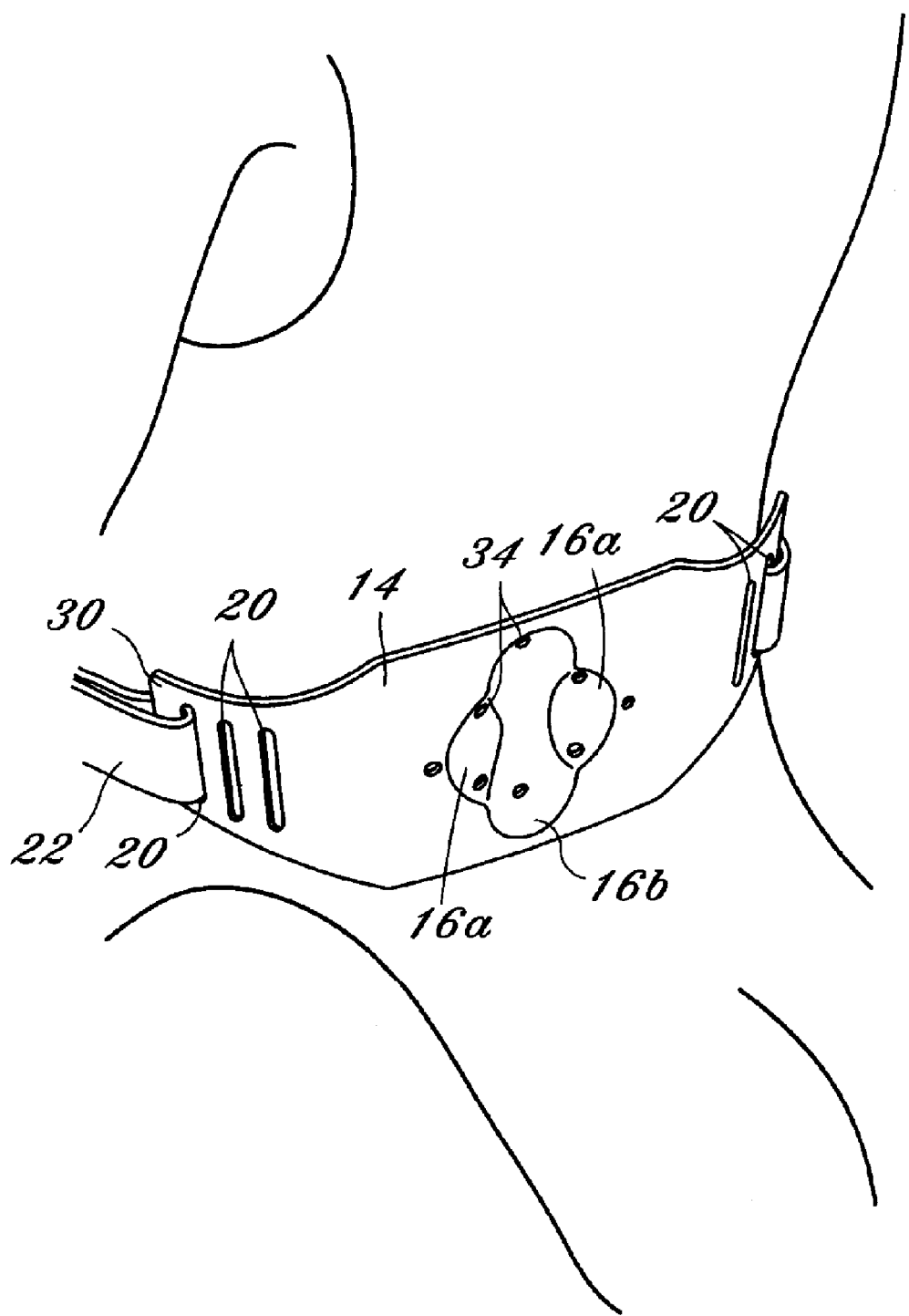
FIG. 6 illustrates a rear perspective view of the lumbar support member as positioned on the lower back of the user.

When looking at the lumbar support member 14 in FIGS. 4A and 4B, the overall shape is somewhat planar and rectangular, resembling the overall shape of the body. However, the lumbar support member 14 includes a centrally-positioned, convex dome 16a that is bisected vertically by an oblong elliptical protrusion 16b of equal height that protrudes into the back lumbar area of the lower lumbar region of the user. Preferably, said dome 16a is approximately 2¾ inches in diameter and said elliptical protrusion 16b is approximately 4¼ inches long and 1½ inches wide where said protrusion connects with said dome. The shape of said lumbar support member provides the ideal lumbar back position and contour at the central portion of lumbar region for supporting both the muscular and spine position in said back region. By using an ideally preformed rigid lumbar support member 14, the back muscles are aligned in the ideal configuration and conformance best suited for the human body to tone the muscles, thereby alleviating muscle strain in the lower back area. Simultaneously, as shown in FIG. 3A, the front abdominal member 12 is somewhat rectangular in shape and having some curvature to fit snugly around the abdominal area to support the abdominal muscles. Each of the support members 12 and 14 is approximately 5 inches high, 12 inches in length, and one-sixteenth inch thick. Said support members 12, 14 are also made from thermal plastic that is basically rigid but which does have a sufficient amount of pliability to provide for comfort and safety. The lumbar support member 14 is somewhat flat in the center with the exception of the circular dome 16a and oblong elliptical protrusion 16b but is curved near the end portions of said support member 14 to protrude around the sides of the individual for comfort.

Several advantages are inherent in the present invention 10, especially with respect to relieving muscle strain in the lower back area. By providing the ideal configuration for the human back as a support guide, the device 10 tones the muscles and aligns the back lumbar region in the proper configuration, thereby training the muscles to be supported in the proper position. At the same time, the abdominal area support member 12 provides a contractive support that provides the proper front muscular support in the abdominal region with the overall result of greatly reducing strain on the lower back area and greatly enhancing muscle tone and realignment of the various lumbar muscles. The device 10 permits the stomach to be pulled in and the stomach to also achieve an appropriate configuration. The depth of the circular dome 16a and oblong elliptical protrusion 16b should be approximately one-fourth to one-half inch so that said dome and said oblong protrusion can nestle in the lower lumbar area of the back. The device 10 can be manufactured in predetermined small, medium, and large sizes because of the vast adjustability of the fastening belts 22 and 24 and can generally fit human beings with waists ranging in size from 25 inches to 54 inches. The belt straps 22 and 24 include some elastic portions 22a and 24a, which are safety precautions to permit some stretch as a benefit to the wearer.

With the tremendous support provided both in the front and back of the body, the device 10 is both comfortable and easily worn during sporting activity, such as golf or tennis, for the benefit of the wearer. In summary, the device 10 provides lumbar and abdominal support with a preformed lumbar support member 14 and preformed abdominal support member 12 that can be snugly affixed to the wearer. The perfect back configuration provided by the device 10 benefits the user by realigning the spinal column while toning and realigning back muscles around the back and spinal column.

The instant invention has been shown and described herein in what is considered to be the most practical and preferred embodiment. The applicant recognizes, however, that departures may be made therefrom within the scope of the invention and that obvious modifications will occur to a person skilled in the art.

What is claimed is:

1. A brace for supporting a user's abdomen and lower back, comprising:
    an abdominal support member, contoured to comfortably support the abdominal region of the user, said member having a first end and a second end, and including a plurality of adjustment slots adjacent to each of said first and second ends;
    a lumbar support member, contoured to comfortably support the lumbar spine region of the user, said member having a first end and a second end, and including a plurality of adjustment slots adjacent to each of said first and second ends;
    said lumbar support member incorporating a convex circular dome having a vertically bisecting oblong elliptical protrusion of equal depth, said circular dome and said oblong protrusion being sized for protrusion into the central lumbar region of the user for supporting and aligning the skeletal and muscular structure of the user's lower back; and
    first and second elastic belts of a connective material attached to said adjustment slots at said first ends and said second ends respectively of said lumbar and said abdominal support members for increasing pressure of said abdominal support member and said lumbar support member against the abdominal and lumbar regions of the user.

2. The brace according to claim 1, wherein said abdominal and lumbar support members are made from thermal plastic, said support members being preformed in anatomically conforming configurations in standard sizes, each sized lumbar support member having a proportionally-sized, protruding circular dome with a vertically bisecting oblong, elliptical protrusion of equal depth, to precisely fit and support the user.

3. The brace according to claim 1, wherein said abdominal and lumbar support members are substantially rectangular and further include rounded tapered edges for preventing unwanted pressure during wear.

4. The brace according to claim 1, wherein said abdominal and lumbar support members include vents for allowing the circulation of air under each respective member.

* * * * *